United States Patent
Kim et al.

(10) Patent No.: US 9,961,304 B2
(45) Date of Patent: May 1, 2018

(54) ULTRASONIC IMAGE PROCESSING APPARATUS AND METHOD

(71) Applicant: SAMSUNG MEDISON CO., LTD., Gangwon-do (KR)

(72) Inventors: Sung Yoon Kim, Namyangju-si (KR); Jun Sang Yoo, Seongnam-si (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 307 days.

(21) Appl. No.: 14/279,083

(22) Filed: May 15, 2014

(65) Prior Publication Data

US 2014/0354776 A1    Dec. 4, 2014

(30) Foreign Application Priority Data

May 30, 2013 (KR) ........................ 10-2013-0061411

(51) Int. Cl.
| | |
|---|---|
| *G06K 9/00* | (2006.01) |
| *H04N 7/18* | (2006.01) |
| *A61B 8/08* | (2006.01) |
| *G06T 7/00* | (2017.01) |
| *G01N 29/06* | (2006.01) |
| *G01N 29/44* | (2006.01) |
| *A61B 8/00* | (2006.01) |

(52) U.S. Cl.
CPC ............... *H04N 7/18* (2013.01); *A61B 8/483* (2013.01); *G01N 29/0654* (2013.01); *G01N 29/44* (2013.01); *G06T 7/0012* (2013.01); *A61B 8/4405* (2013.01); *G01N 2291/02475* (2013.01); *G06T 2207/10136* (2013.01); *G06T 2207/30044* (2013.01)

(58) Field of Classification Search
None
See application file for complete search history.

(56) References Cited

U.S. PATENT DOCUMENTS

| | | | | |
|---|---|---|---|---|
| 6,277,372 | B1 * | 8/2001 | Fraser | A61K 35/30 424/93.1 |
| 8,055,324 | B1 * | 11/2011 | Parker | A61B 8/465 600/407 |
| 2001/0049827 | A1 * | 12/2001 | Hunter | A01K 67/027 800/8 |

(Continued)

OTHER PUBLICATIONS

Adam A, , "Mesh Voxelisation", Feb. 13, 2013, Mathwork, http://www.mathworks.com/matlabcentral/fileexchange/27390-mesh-voxelisation.*

*Primary Examiner* — Randolph I Chu
(74) *Attorney, Agent, or Firm* — McDermott Will & Emery LLP

(57) ABSTRACT

Disclosed herein is an ultrasonic image processing method and apparatus. The ultrasonic image processing method includes acquiring volume data by radiating ultrasonic waves to an area around the uterus, extracting at least one object candidate group based on the acquired volume data, and displaying the at least one extracted object candidate group on a screen. The ultrasonic image processing apparatus includes a data acquisition unit acquiring volume data of an area around the uterus using ultrasonic waves, a data processing unit extracting at least one object candidate group based on the acquired volume data, and a display unit displaying the at least one extracted object candidate group on a screen.

16 Claims, 15 Drawing Sheets

(56) References Cited

U.S. PATENT DOCUMENTS

| | | | |
|---|---|---|---|
| 2007/0269411 A1* | 11/2007 | Sun | C12N 15/86 |
| | | | 424/93.2 |
| 2010/0040614 A1* | 2/2010 | Ahmed | A61K 39/12 |
| | | | 424/133.1 |
| 2010/0191114 A1* | 7/2010 | Hyun | A61B 8/00 |
| | | | 600/443 |
| 2011/0040170 A1* | 2/2011 | Geva | A61B 18/22 |
| | | | 600/411 |
| 2011/0118598 A1* | 5/2011 | Gertner | A61B 8/06 |
| | | | 600/431 |
| 2011/0165072 A1* | 7/2011 | Gold | A61K 47/48746 |
| | | | 424/1.49 |
| 2011/0200678 A1* | 8/2011 | Hwang | B01J 2/04 |
| | | | 424/489 |
| 2012/0035462 A1* | 2/2012 | Maurer, Jr. | A61B 8/4245 |
| | | | 600/411 |
| 2015/0173650 A1* | 6/2015 | Yoo | G06T 7/602 |
| | | | 600/443 |
| 2015/0328346 A1* | 11/2015 | Harmsen | A61K 49/0093 |
| | | | 424/1.37 |

* cited by examiner

ULTRASONIC IMAGE PROCESSING APPARATUS AND METHOD

CROSS-REFERENCE TO RELATED APPLICATION

This application claims the benefit of Korean Patent Application No. 2013-0061411, filed on May 30, 2013 in the Korean Intellectual Property Office, the disclosure of which is incorporated herein by reference.

BACKGROUND

1. Field

Embodiments of the present invention relate to an apparatus and method of imaging ultrasonic signals.

2. Description of the Related Art

In general, an ultrasonic diagnostic apparatus radiates ultrasonic signals to a specific region of the inside of the body of an object from the surface of the body of the object, and non-invasively acquires tomographic images or images regarding blood pressure of soft tissues using reflected ultrasonic signals (ultrasonic echo signals).

As compared to other image diagnostic apparatuses, such as an X-ray diagnostic apparatus, a computed tomography (CT) scanner, a magnetic resonance imaging (MRI) apparatus, and a nuclear medicine diagnostic apparatus, the ultrasonic diagnostic apparatus is small and inexpensive, displays images in real time, and has high safety without X-ray exposure. Due to these advantages, the ultrasonic diagnostic apparatus is used for diagnosis of the heart, the breast, the abdomen, and the renal system.

Particularly, the ultrasonic diagnostic apparatus is widely used for diagnosis in obstetrics and gynecology because the ultrasonic diagnostic apparatus may be used to check the health of a fetus within a pregnant woman and to confirm whether or not environments around the fetus are proper to maintain the health of the fetus and the pregnant woman. Through check of the state of the uterus of the pregnant woman in which the fetus is placed, healthy delivery of the baby is facilitated.

SUMMARY

Therefore, it is an aspect of the present invention to provide an apparatus and method of imaging ultrasonic signals.

Additional aspects of the invention will be set forth in part in the description which follows and, in part, will be obvious from the description, or may be learned by practice of the invention.

In accordance with one aspect of the present invention, an ultrasonic image processing method includes acquiring volume data by radiating ultrasonic waves to an area around the uterus, extracting at least one object candidate group based on the acquired volume data, and displaying the at least one extracted object candidate group on a screen.

In the acquisition of the volume data, the area around the uterus where the volume data is acquired may be set.

The acquisition of the volume data may be carried out using one of a matrix probe, a 3D probe, and a hands-free 3D probe.

The acquisition of the volume data may include acquiring 4D data using the acquired volume data.

The extraction of the at least one object candidate group, if a plurality of object candidate groups are extracted, may include determining accuracy rankings of the extracted object candidate groups.

The display of the at least one extracted object candidate group on the screen may include displaying the determined rankings on the screen.

The display of the determined rankings on the screen may be performed using one of numbers, color, and a table The display of the at least one extracted object candidate group on the screen may be performed through one of a method of displaying the at least one extracted object candidate group on the screen by directly marking the at least one extracted object candidate group in an ultrasonic image, a method of extracting the at least one extracted object candidate group from an ultrasonic image and displaying the at least one extracted object candidate group separately from the ultrasonic image, and a method of displaying the at least one extracted object candidate group using different rendering.

The display of the at least one extracted object candidate group on the screen may include 2-dimensionally or 3-dimensionally displaying the at least one extracted object candidate group.

The ultrasonic image processing method may further include selecting an object candidate group from the displayed object candidate groups through input, and displaying measured data of the selected object candidate group.

The ultrasonic image processing method may further include displaying measured data of the displayed object candidate groups, and selecting an object candidate group from the displayed object candidate groups through input.

The input may be applied by a user at the outside of an ultrasonic image processing apparatus or be applied by arithmetic operation within the ultrasonic image processing apparatus.

In the selection of the object candidate group, at least one object candidate group may be selected.

The measured data may include volumes, lengths, and shapes of display items of the object candidate group.

The display items of the object candidate group may include a G-sac, a Y-sac, an amniotic sac, and a CRL.

The display items may be selected by a user at the outside of an ultrasonic image processing apparatus or be selected by arithmetic operation within the ultrasonic image processing apparatus.

The display of the measured data may include acquiring and displaying one of a GA, an EDD, and a risk degree of a pregnant woman based on the measured data.

In accordance with another aspect of the present invention, an ultrasonic image processing apparatus includes a data acquisition unit acquiring volume data of an area around the uterus using ultrasonic waves, a data processing unit extracting at least one object candidate group based on the acquired volume data, and a display unit displaying the at least one extracted object candidate group on a screen.

The ultrasonic image processing apparatus may further include an input unit sensing input to select at least one object candidate group from the at least one displayed object candidate group.

The display unit may display measured data of the at least one selected object candidate group according to the sensed input.

The display unit may display measured data of the at least one displayed object candidate group.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1:
FIG. 1 is a view illustrating one example of a 2D ultrasonic image of the inside of the uterus.

Reference will now be made in detail to the embodiments of the present invention, examples of which are illustrated in the accompanying drawings, wherein like reference numerals refer to like elements throughout.

Ectopic pregnancy means pregnancy in which a fertilized egg is not normally implanted into the cavity of the uterus but is abnormally implanted into other places around the uterus. Ectopic pregnancy is generally generated by damage to the fallopian tubes, and is mainly caused by damage to the fallopian tubes due to inflammation or infection or physical damage to the fallopian tubes due to tubal surgery. Ectopic pregnancy may be caused by confinement of a fertilized egg within a diverticulum of the fallopian tube or obstruction to progress of a fertilized egg to the uterus.

Particularly, as women grow older, in vitro fertilization and artificial insemination become increasingly popular. Thereby, a multifetal pregnancy rate increases and thus the likelihood of ectopic pregnancy also increases.

Ectopic pregnancy manifests as a variety of clinical symptoms. In general, ectopic pregnancy patients experience menstrual dysfunction or suffer spontaneous abortion. Further, ectopic pregnancy patients commonly complain about bleeding and lower abdominal pain, and levels of the bleeding and pain may vary. Sometimes, ectopic pregnancy patients complain of dizziness or neck or shoulder pain. Particularly, as the fetus develops, rupture of organs surrounding the ectopic fetus becomes an issue. This causes severe bleeding and possibly loss of life. As such, it is important to detect ectopic pregnancy in the early stages so that proper measures can be taken.

Hereinafter, with reference to FIGS. 1 and 2, a conventional method of confirming ectopic pregnancy and problems associated therewith will be described.

FIG. 1 is a view illustrating one example of a 2D ultrasonic image of the inside of the uterus. An ultrasonic diagnostic method is mainly used to confirm pregnancy. In the case of general pregnancy, existence of a G-Sac may be confirmed by inspecting the inside of the uterus through diagnosis using transvaginal ultrasonography. An ultrasonic probe used in general diagnosis using transvaginal ultrasonography employs a 1D array probe. Therethrough, the 2D ultrasonic image shown in FIG. 1 may be acquired. The G-sac means a gestational sac and refers to a fertilized egg consisting of a decidua and a ciliary membrane, the outer circumference of which increases during pregnancy. Therefore, when the G-sac is confirmed through uterine diagnosis using ultrasonography, it may be judged that a person to be diagnosed is pregnant.

However, in case of ectopic pregnancy, it is difficult to find a G-sac through uterine diagnosis using the 1D array probe shown in FIG. 1. The reason for this is that only the inside of the uterus is inspected through ultrasonic diagnosis. In this case, ectopic pregnancy is diagnosed through blood inspection, i.e., by detecting whether or not the concentration of serum β-hCG is more than 1,500 mIU/ml. In order to confirm ectopic pregnancy, a separate diagnostic method, such as blood inspection, is additionally performed and, thus, additional costs and time are required and a patient may have difficulty in maintaining mental and physical stability. Therefore, a method of detecting the G-sac in the early stages is required.

Figure 2:
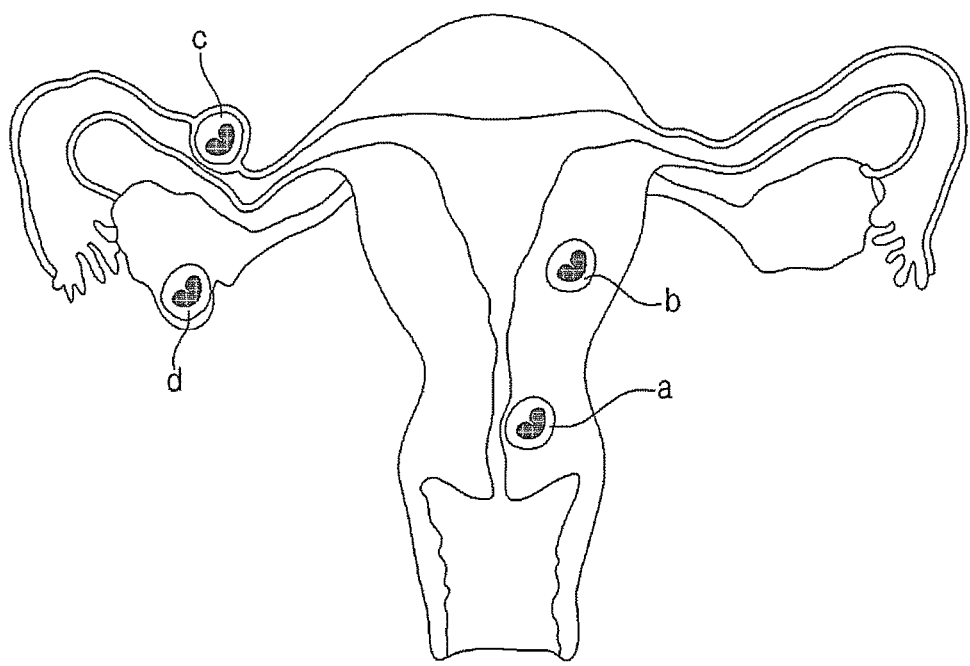
FIG. 2 is a view illustrating positions around the uterus where ectopic pregnancy is possible.

FIG. 2 is a view illustrating positions around the uterus where ectopic pregnancy is possible. In FIG. 2, a represents a case in which a fertilized egg is implanted into the cervix of the uterus, b represents a case in which a fertilized egg is implanted into the myometrium of the uterus, c represents a case in which a fertilized egg is implanted into the fallopian tube of the uterus, and d represents a case in which a fertilized egg is implanted into the ovarium. Since the fertilized egg is implanted into a position which is not found through general diagnosis using transvaginal ultrasonography in which only the inside of the uterus is inspected, it may be difficult to diagnose ectopic pregnancy in the early stages.

Ectopic pregnancy is mainly caused by implantation of a fertilized egg into the fallopian tube of the uterus, through which the ovum emitted from the ovarium is conveyed to the uterus. In addition, ectopic pregnancy may be caused by implantation of a fertilized egg into various ligaments supporting the ovarium generating the ovum or the uterus, the abdominal cavity, or the cervix of the uterus. Therefore, confirmation of existence of a G-sac at an area around the uterus as well as at the inside of the uterus through ultrasonic diagnosis is required.

Figure 3:
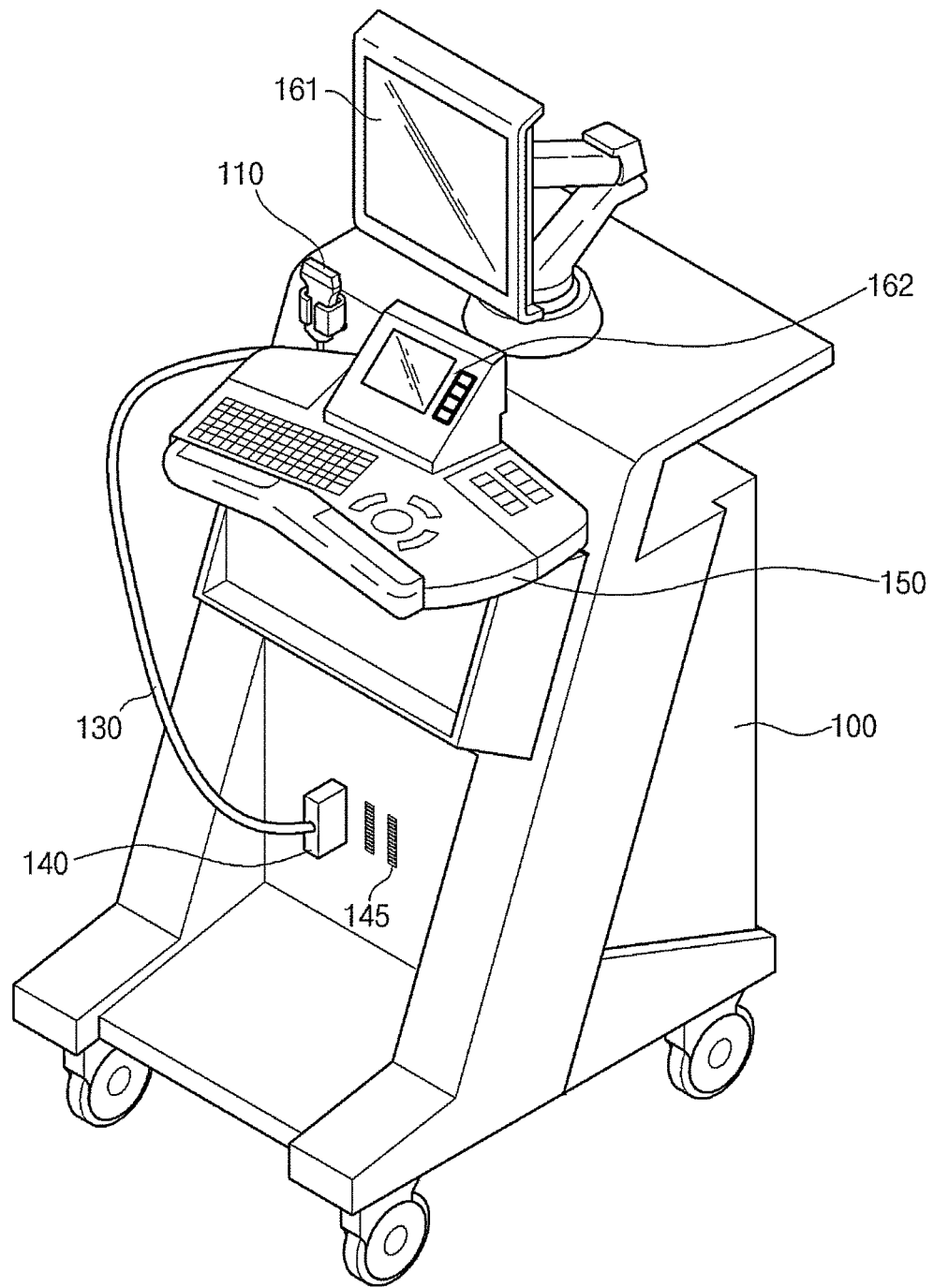
FIG. 3 is a perspective view illustrating an ultrasonic image processing apparatus in accordance with one embodiment of the present invention.

FIG. 3 is a perspective view illustrating an ultrasonic image processing apparatus in accordance with one embodiment of the present invention. As exemplarily shown in FIG. 3, the ultrasonic image processing apparatus may include a main body 100, a data acquisition unit 110, an input unit 150, a main display 161, and a sub-display 162.

At least one female connector 145 may be provided at one side of the main body 100. A male connector 140 connected to a cable 130 may be physically combined with the female connector 145.

A plurality of casters (not shown) for mobility of the ultrasonic image processing apparatus may be provided at the lower portion of the main body 100. The plural casters may fix the ultrasonic image processing apparatus in a specific place or allow the ultrasonic image processing apparatus to move in a specific direction.

The data acquisition unit 110 contacts the surface of the body of an object, and may transmit and receive ultrasonic waves. In more detail, the data acquisition unit 110 serves to transmit a transmission signal provided from the main body 110, i.e., an ultrasonic signal, to the inside of the body of the object, and to receive an ultrasonic echo signal reflected by a specific region of the inside of the body of the object and transmit the received ultrasonic echo signal to the main body 100. One end of the cable 130 may be connected to the data acquisition unit 110, and the male connector 140 may be connected to the other end of the cable 130. The male connector 140 connected to the other end of the cable 130 may be physically combined with the female connector 145 of the main body 100.

The input unit 150 receives instructions regarding operation of the ultrasonic image processing apparatus. For example, the input unit 150 may receive mode selection instructions to select one of an amplitude mode (A-mode), a brightness mode (B-mode), and a motion mode (M-mode), or an ultrasonic diagnosis start instructions. Instructions inputted through the input unit 150 may be transmitted to the main body 100 through wired communication or wireless communication.

The input unit 150 may include, for example, at least one of a keyboard, a foot switch, and a foot pedal. As one example, the keyboard may be implemented with hardware and located on the main body 100. Such a keyboard may include at least one of switches, a key, a joystick, and a track ball. As another example, the keyboard may be implemented with software, such as a graphical user interface. In this case, the keyboard may be displayed through the sub-display 162 or the main display 161. The foot switch or the foot pedal may be provided at the lower portion of the main body 100, and an operator may control operation of the ultrasonic image processing apparatus using the foot pedal.

A display unit 160 may include the main display 161 and the sub-display 162. The sub-display 162 may be provided on the main body 100. FIG. 3 illustrates the sub-display 162 as being provided at the upper portion of the input unit 150. The sub-display 162 may display applications regarding operation of the ultrasonic image processing apparatus. For example, the sub-display 162 may display a menu or guidance necessary for ultrasonic diagnosis. For example, the sub-display 162 may include a cathode ray tube (CRT) or a liquid crystal display (LCD).

The main display 161 may be provided on the main body 100. FIG. 3 illustrates the main display 161 as being provided above the sub-display 162. The main display 161 may display an ultrasonic image acquired during an ultrasonic diagnosis process. The main display 161 may include a cathode ray tube (CRT) or a liquid crystal display (LCD), in the same manner as the sub-display 162. Although FIG. 3 illustrates the main display 161 as being combined with the main body 100, the main display 161 may be configured such that it is separable from the main body 100.

Although FIG. 3 illustrates the ultrasonic image processing apparatus as including both the main display 161 and the sub-display 162, the sub-display 162 may be omitted as needed. In this case, the applications or menu displayed through the sub-display 162 may be displayed through the main display 161.

Figure 4:
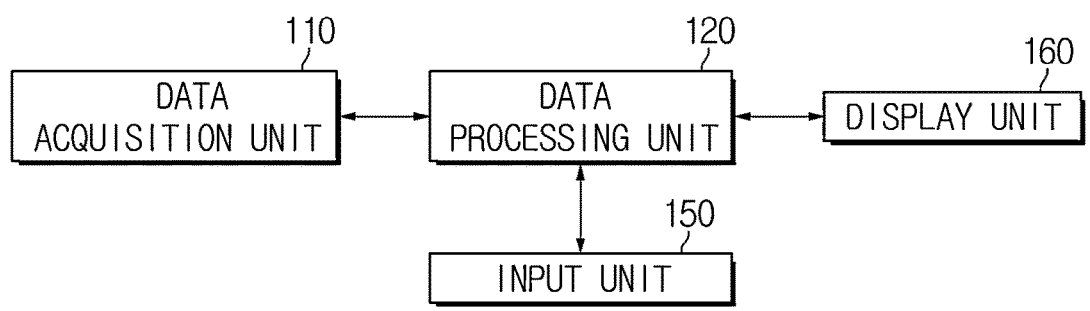
FIG. 4 is a control block diagram of the ultrasonic image processing apparatus in accordance with the embodiment of the present invention.

FIG. 4 is a control block diagram of the ultrasonic image processing apparatus in accordance with the embodiment of the present invention.

The data acquisition unit 110 may collect data of an object by radiating ultrasonic waves. The data acquisition unit 110 includes a plurality of ultrasonic transducers generating ultrasonic waves according to AC current applied from a power supply, radiating the ultrasonic waves to the object, receiving ultrasonic echo waves reflected by a target region of the inside of the object, and converting the ultrasonic echo waves into electrical signals. Here, the power supply may be an external power supply device or an electricity storage device within the ultrasonic image processing apparatus.

When AC current is applied from the power supply to the plural ultrasonic transducers, piezoelectric vibrators or thin films of the ultrasonic transducers are vibrated, and as a result, ultrasonic waves are generated. The generated ultrasonic waves are radiated to an object, for example, the inside of a human body. The radiated ultrasonic waves are reflected by at least one target region located at various depths within the object. The ultrasonic transducers receive ultrasonic echo signals reflected by the target region, and acquire a plurality of reception signals by converting the received ultrasonic echo signals into electrical signals.

The data acquisition unit 110 may acquire 3D volume data of an area around the uterus during ultrasonic diagnosis of a pregnant woman. Since a fertilized egg may be implanted into an area around the uterus as well as the inside of the uterus, as exemplarily shown in FIG. 2, whether or not ectopic pregnancy occurs may be confirmed by acquiring 3D volume data of the area around the uterus including the inside of the uterus. Therefore, the data acquisition unit 110 may include a matrix probe, a 3D probe, or a hands-free 3D probe, which easily acquires volume data.

In an ultrasonic image processing method in accordance with one embodiment of the present invention, not only the volume data acquired by the data acquisition unit 110 may be processed but also 4D data based on the volume data may be acquired and processed. That is, the volume data acquired by the data acquisition unit 110 is transmitted to the main body 100 in real time and is thus processed, and an ultrasonic image may be displayed on the display unit 160 in real time.

The range of an area around the uterus from which the data acquisition unit 110 will acquire volume data may be separately set. The reason for this is that, when the area around the uterus where pregnancy is possible as well as the inside of the uterus is properly set, as exemplarily shown in FIG. 2, whether or not ectopic pregnancy occurs may be confirmed. The range of the area around the uterus may be set by controlling a scan angle and a scan depth. Such settings may be carried out through separate input by a user using the input unit 150 of the ultrasonic image processing apparatus, or may be arbitrarily set by arithmetic operation within the ultrasonic image processing apparatus.

A data processing unit 120 may receive volume data of an area around the uterus from the data acquisition unit 110. The data processing unit 120 performs rendering, i.e., conversion of the received volume data into an ultrasonic image. Furthermore, the data processing unit 120 may perform detection of object candidate groups based on the received volume data. The object candidate groups mean forms having brightness or shape suspected to be a fertilized egg. A suspected case means that, when a form is compared to a general fertilized egg in an ultrasonic image using brightness or shape of the general fertilized egg as a reference value, the form is similar to the general fertilized egg within a designated range.

When the brightness of shape value of a general fertilized egg are used as a reference value, the reference value may be stored in advance in the ultrasonic image processing apparatus, or a reference value at the outside of the ultrasonic image processing apparatus may be read and used. Further, a similarity degree of the value of a form as the reference value may be set by the inside or outside of the ultrasonic image processing apparatus.

The data processing unit 120 may extract a plurality of object candidate groups suspected to be an object. Among the extracted plural object candidate groups, an object candidate group having a brightness or shape value closer to the reference value has a higher likelihood of being the object. Therefore, proximity degrees of the brightness or shape values of the object candidate groups to the reference value may be measured, and accuracy rankings may be determined in order of the proximity degrees. When the rankings of the object candidate groups are determined, more accurate object detection is facilitated in ultrasonic diagnosis.

The display unit 160 receives information of the object candidate groups extracted by the data processing unit 120. Further, the display unit 160 may display the object candidate groups based on the received information.

Figure 5:
FIG. 5 is a view illustrating one example of an ultrasonic image around the uterus based on volume data.

FIG. 5 is a view illustrating one example of an ultrasonic image around the uterus based on volume data. Since the data acquisition unit 110 acquires volume data of an area around the uterus, an image outputted from the display unit 160 may be a 3D ultrasonic image. Further, since the volume data is acquired by combining a plurality of tomographic data, the display unit 160 may display a 2D tomographic image. Hereinafter, it will be assumed that the display unit 160 displays a tomographic image of an area, desired by a user, around the uterus among the acquired volume data.

Figure 6:
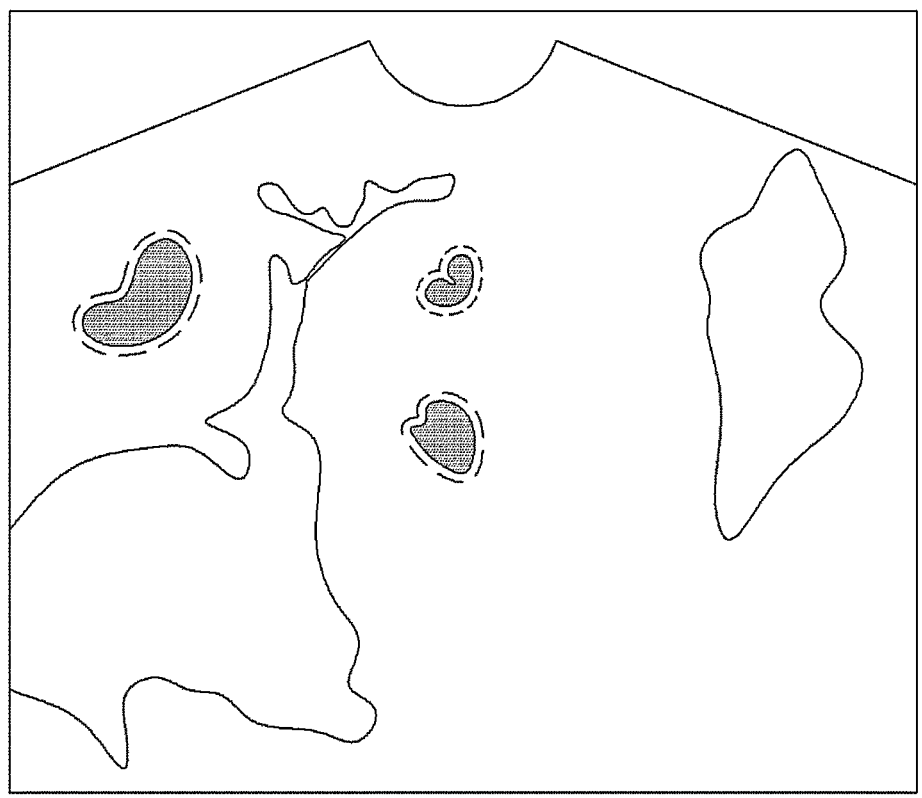
FIG. 6 is a view illustrating one example of a method of displaying object candidate groups by dividing the object candidate groups from an ultrasonic image, among methods of displaying object candidate groups.

FIG. 6 is a view illustrating one example of a method of displaying object candidate groups by dividing the object candidate groups from an ultrasonic image, among methods of displaying object candidate groups. As described above, in the ultrasonic image processing apparatus in accordance with the embodiment of the present invention, the display unit 160 may receive information regarding object candidate groups from the data processing unit 120. However, in order to display the object candidate groups while displaying an ultrasonic image using the volume data, separate processing divided from the background ultrasonic image is required.

FIG. 6 illustrates one example of a method of displaying object candidate groups by directly marking the object candidate groups in the ultrasonic image. Marking is carried out along the boundaries of the respective object candidate groups and, thus, the object candidate groups may be easily visually divided from the ultrasonic image during ultrasonic diagnosis.

However, the method of displaying object candidate groups by dividing the object candidate groups from an ultrasonic image is not limited thereto. That is, object candidate groups may be extracted from an ultrasonic image around the uterus and be displayed separately from the ultrasonic image, or object candidate groups may be processed through rendering different from rendering performed to display the volume data of an area around the uterus, for example, a method of varying OTF during rendering or a method using early ray termination, and be displayed. The shapes of displayed object candidate groups are different according to the above respective methods and, thus, the above plural methods may be carried out together.

Figure 7:
FIG. 7 is a view illustrating one example of a method of displaying object candidate groups together with accuracy rankings, among methods of displaying object candidate groups.

FIG. 7 is a view illustrating one example of a method of displaying object candidate groups together with accuracy rankings, among methods of displaying object candidate groups. In the ultrasonic image processing apparatus in accordance with the embodiment of the present invention, the display unit 160 may receive accuracy rankings of object candidate groups from the data processing unit 120. Therefore, the display unit 160 may display the received rankings together with the object candidate groups.

The display unit 160 may display the accuracy rankings of the object candidate groups, determined by the data processing unit 120, through various methods. Although FIG. 7 illustrates display of accuracy rankings of the respective object candidate groups with numbers, the method of displaying object candidate groups together with accuracy rankings is not limited thereto. The accuracy rankings of the object candidate groups may be displayed through change of color according to the rankings, or the accuracy rankings of the object candidate groups may be displayed through a table provided separately from display of the object candidate groups.

Figure 8:
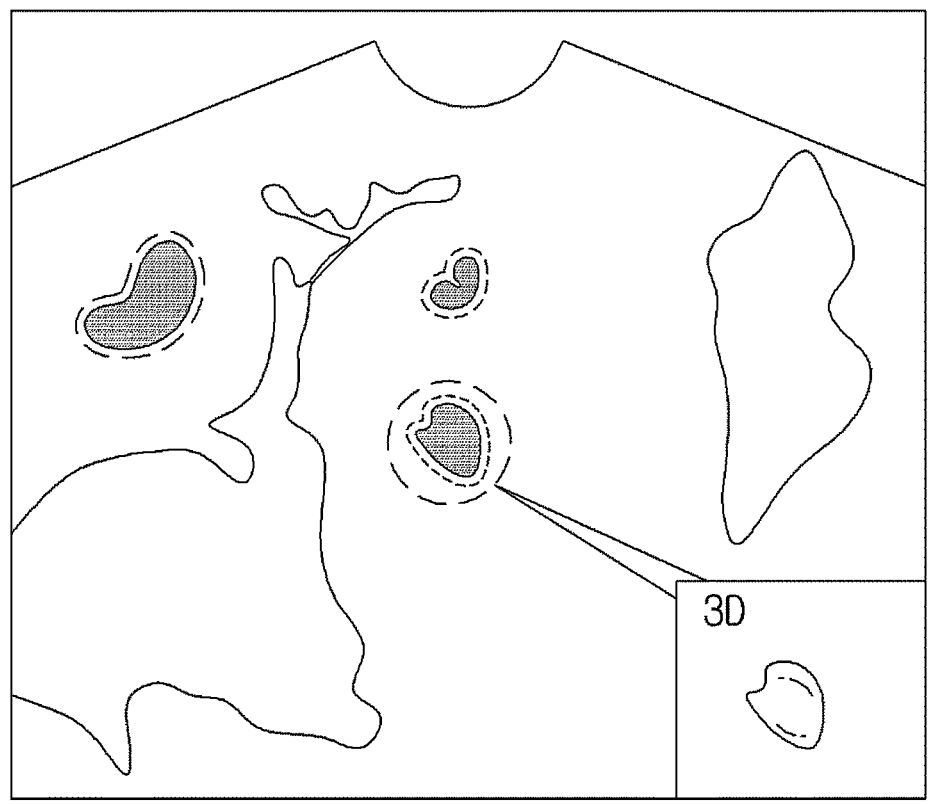
FIG. 8 is a view illustrating one example of a method of 3-dimensionally displaying object candidate groups, among methods of displaying object candidate groups.

FIG. 8 is a view illustrating one example of a method of 3-dimensionally displaying object candidate groups, among methods of displaying object candidate groups. The display unit 160 may display 3D images of the object candidate groups together with display of a 2D ultrasonic image of the uterus. The display unit 160 may receive a 3D ultrasonic image, acquired from the data processing unit 120 through volume rendering of volume data, and display the 3D ultrasonic image, and receive a 2D ultrasonic image of a specific cross-section of volume data from the data processing unit 120 and display the 2D ultrasonic image. Therefore, the display unit 160 may display a 2D or 3D ultrasonic image by user selection or arithmetic operation within the apparatus.

FIG. 8 illustrates a 3D image of a specific object candidate group in the 2D ultrasonic image. If a user wants to select one of plural object candidate groups, more accurate selection of the user may be facilitated by confirming 3D ultrasonic images of the respective object candidate groups.

Differently from FIG. 8, 2D sectional images of object candidate groups in a 3D ultrasonic image around the uterus may be confirmed, or tomographic images having different depths in a 3D ultrasonic image of an object candidate group may be confirmed.

If a plurality of object candidate groups is displayed on the display unit 160, the display unit 160 may display information regarding the entirety of the object candidate groups or a selected object candidate group. Information regarding the object candidate groups means data measured according to display items of the object candidate groups. Here, the display items of each object candidate group are acquired by itemizing components in a fertilized egg, if each object candidate group is assumed to be a fertilized egg.

Figure 9:
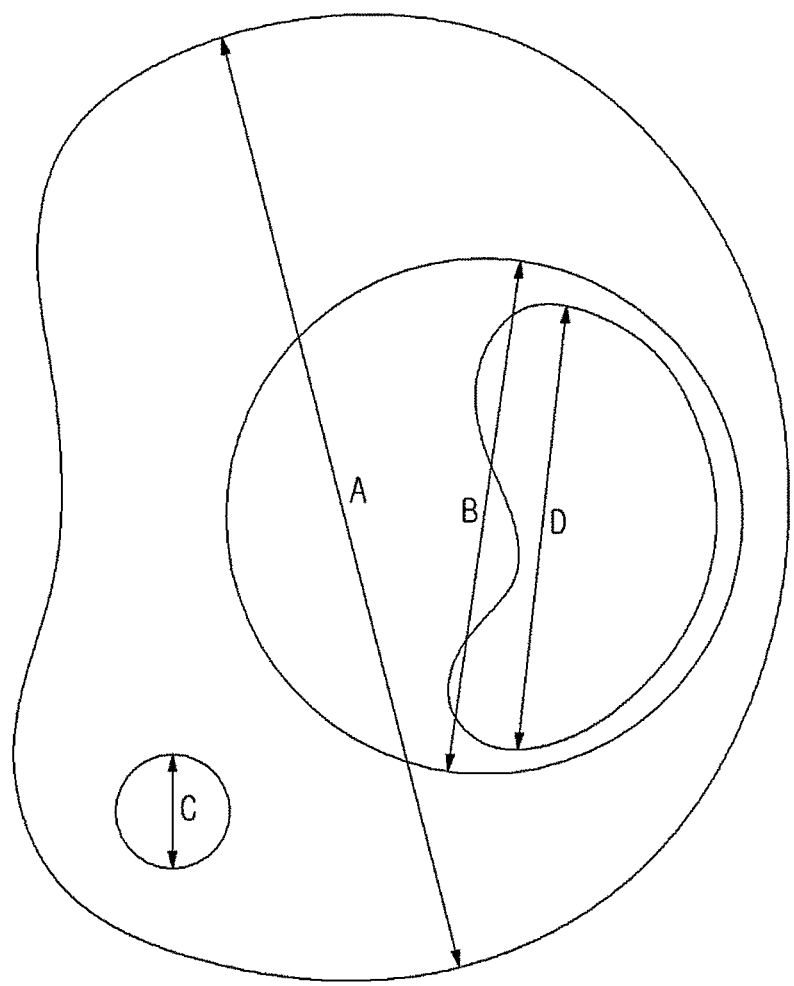
FIG. 9 is a view illustrating the internal structure of a fertilized egg.

FIG. 9 is a view illustrating the internal structure of a fertilized egg. Within the fertilized egg, a G-sac, a Y-sac, an amniotic sac, etc. are present. In FIG. 9, A means the length of the G-sac, and B means the length of the amniotic sac. Further, C means the length of the Y-sac, and D refers to a crown-rump length (CRL), i.e., the distance from the crown to the rump of a fetus. Data of the respective components present within the fertilized egg may be formed by measuring volumes, lengths, and shapes of the components, and such data may be used in ultrasonic diagnosis.

Figure 10:
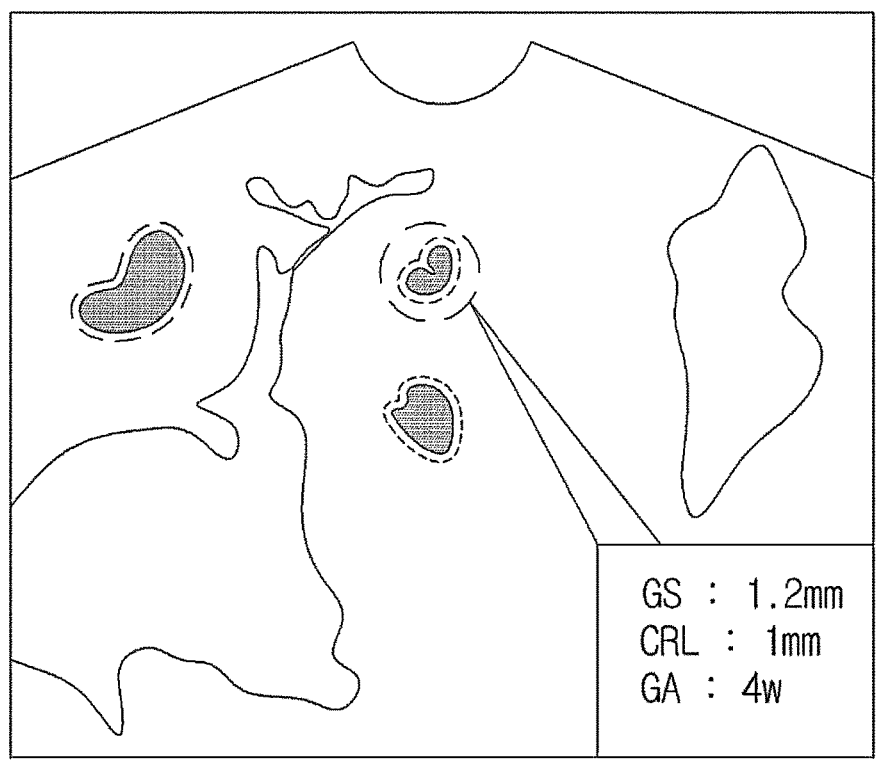
FIG. 10 is a view illustrating one example of a screen displaying measured data according to display items of a selected object candidate group together with the selected object candidate group.

FIG. 10 is a view illustrating one example of a screen displaying measured data according to display items of a selected object candidate group together with the selected object candidate group. As described above, three object candidate groups are present on the screen. A user may select one or more from the three object candidate groups. The display unit 160 may display measured data according to display items of the selected object candidate group. In the example of FIG. 10, the length of the G-sac of the selected object candidate group is 1.2 mm, and the CRL of the selected object candidate group is 1 mm.

Based on these measured data, a GA or an EDD may also be displayed. Here, the GA means a gestational age, and the EDD means an expected date of delivery. Conventionally, a doctor estimates a GA or an EDD through clinical judgment. However, if a GA or an EDD is estimated using measured data according to acquired display items, more accurate information may be transmitted to a user. Based on the measured data of the selected object candidate group shown in FIG. 10, it is judged that a pregnant woman has reached the fourth week in pregnancy.

Further, the display unit 160 may also display a risk degree. The reason for this is that the risk degree of a pregnant woman or a fetus may vary according to a position of a selected object. The risk degree of the pregnant woman or the fetus may be measured based on a distance of the object from the uterus, a position of the object, or the measured data of the object, and the display unit 160 may display acquired results. Such a process may help a user to adjust a time to cope with a problem in consideration of the risk degree of the pregnant woman.

Figure 11:
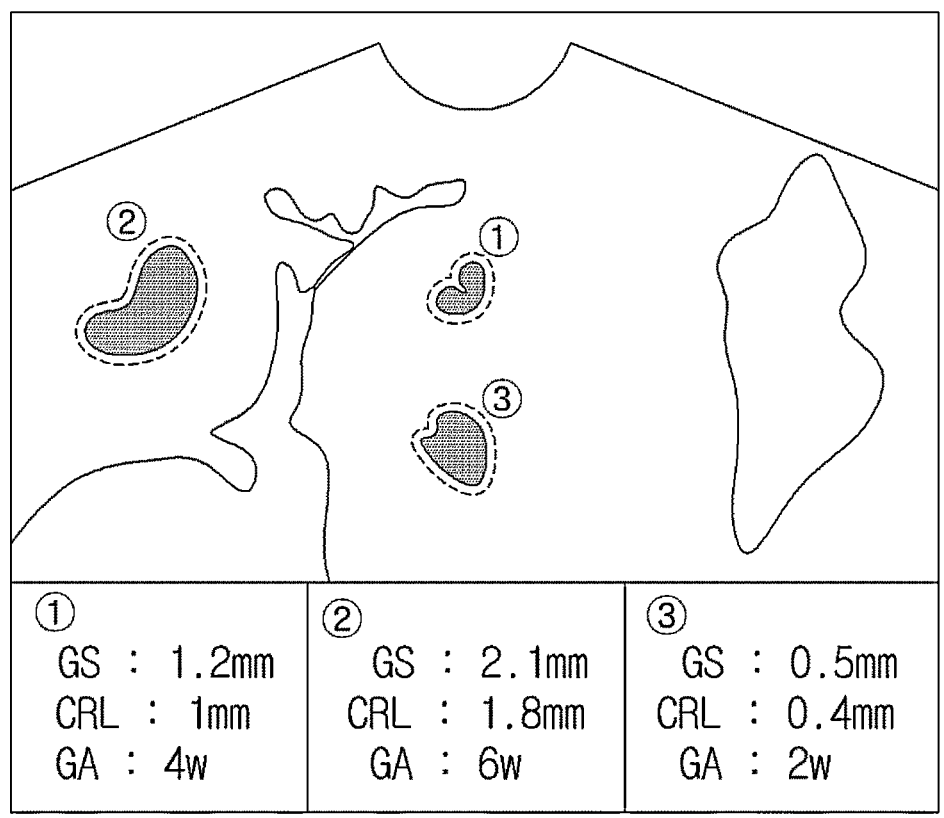
FIG. 11 is a view illustrating one example of a screen displaying measured data according to display items of a plurality of object candidate groups together with the plurality of object candidate groups.

FIG. 11 is a view illustrating one example of a screen displaying measured data according to display items of a plurality of object candidate groups together with the plurality of object candidate groups. Differently from the case of FIG. 10, measured data of all object candidate groups may be displayed prior to selection of an object candidate group. In the example of FIG. 11, numbers according to accuracy rankings of the object candidate groups are displayed and measured data are displayed at the lower end of the screen in order of these numbers.

Measurement and digitization of components within a fertilized egg through various methods and application of acquired data to ultrasonic diagnosis have been described above. Similarly, various measured data of display items of the object candidate groups may be acquired. An object candidate group more proximate to an object is confirmed by comparing the measured data of the object candidate groups with measured data of an actual fertilized egg and thus accuracy in selection of the object candidate group may be increased.

Figure 12:
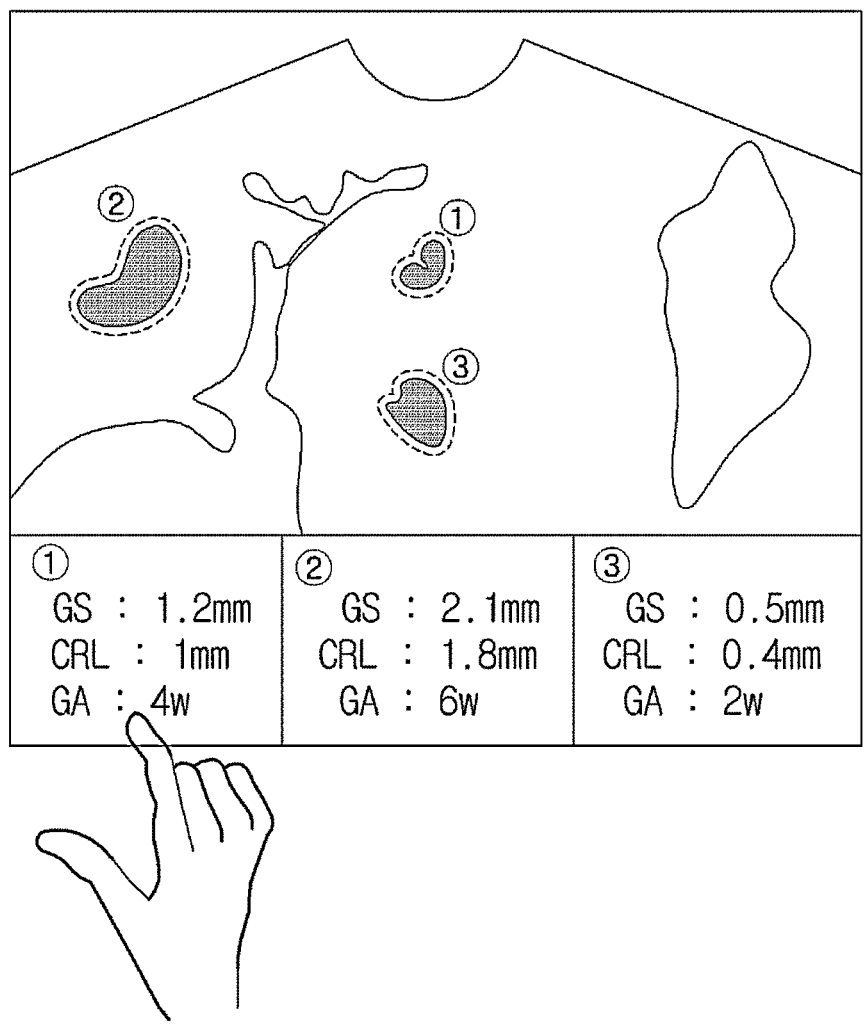
FIG. 12 is a view illustrating a method of selecting one object candidate group on a screen displaying a plurality of object candidate groups by a user in accordance with one embodiment of the present invention.

FIG. 12 is a view illustrating a method of selecting one object candidate group on a screen displaying a plurality of object candidate groups by a user in accordance with one embodiment of the present invention. Here, the user selects object candidate group ① as an object with reference to measured data of the respective object candidate groups and GA values thereof. If an object is selected in consideration of measured data in addition to judgment of accuracy based on brightness or shape of the object, more accurate ultrasonic diagnosis may be facilitated.

Although FIG. 12 illustrates a method of selecting one of the object candidate groups through external input by the user, embodiments of the present invention are not limited thereto. That is, the object candidate group having a measured data value the most proximate to the value of the fertilized egg through arithmetic operation in the ultrasonic image processing apparatus may be selected as an object. Further, one or more object candidate groups may be selected as objects.

Figure 13:
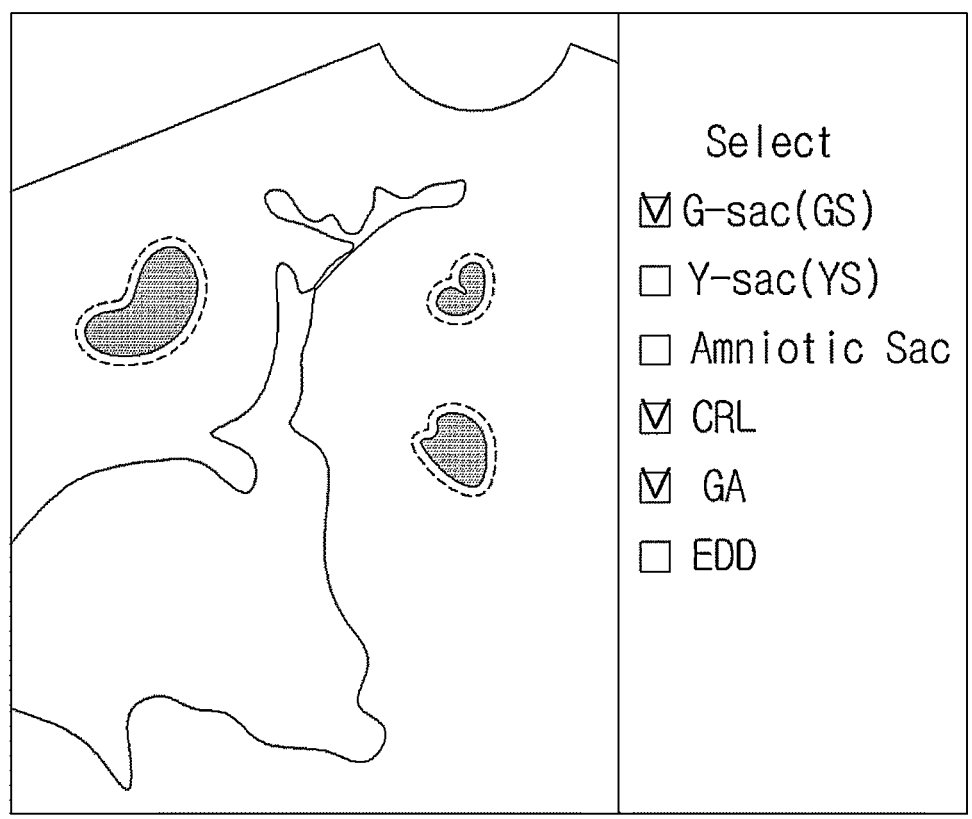
FIG. 13 is a view illustrating one example of a screen on which display items of object candidate groups to be displayed are selected.

FIG. 13 is a view illustrating a screen on which display items of object candidate groups to be displayed are selected in accordance with one embodiment of the present invention. Whether or not the above-described display items of object candidate groups and relating information, such as a GA, an EDD, and a risk degree, will be displayed may be determined by selection. In accordance with the embodiment of FIG. 13, it may be understood that only the G-sac, the CRL, and the GA are selected. In this case, only information regarding the G-sacs, the CRLs, and the Gas of object candidate groups may be displayed Information of the object candidate groups to be displayed may be input through the input unit by a user in this manner, or items arbitrarily selected by arithmetic operation within the apparatus may be displayed.

Figure 14:
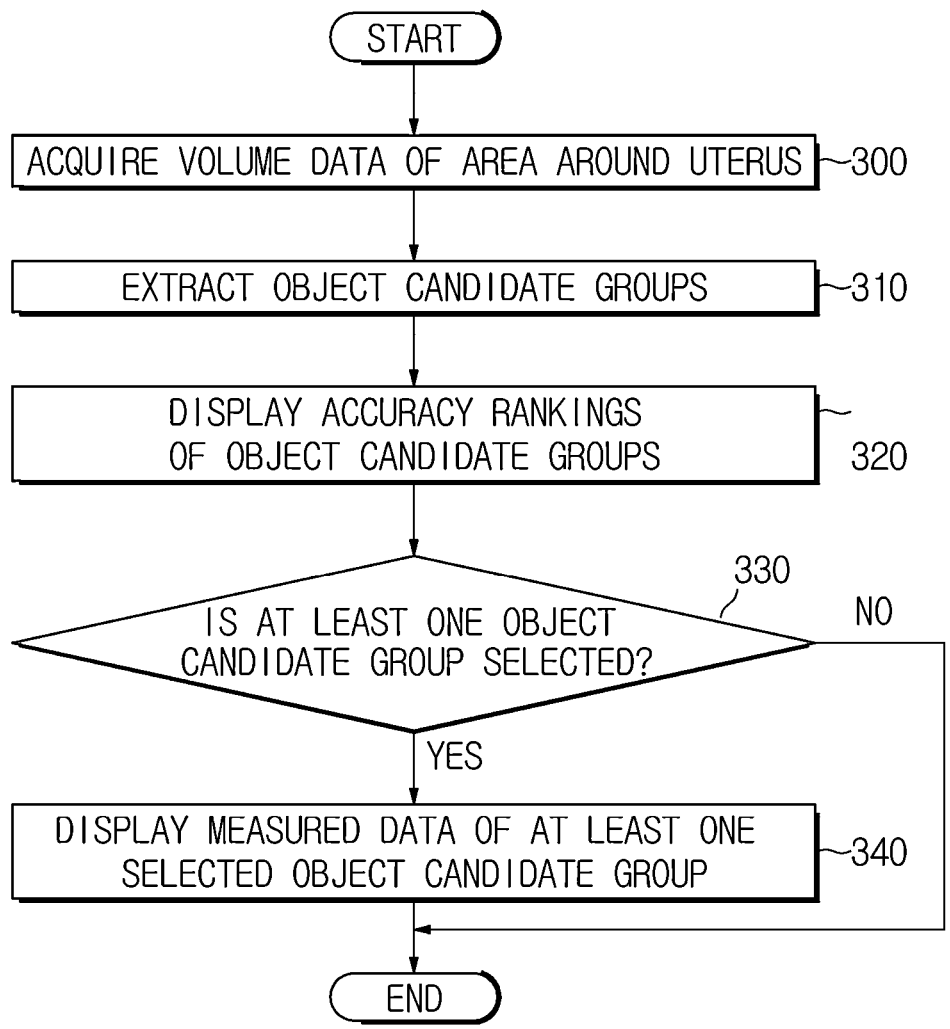
FIG. 14 is a flowchart illustrating an ultrasonic image processing method in which, when an object candidate group is selected, measured data of the selected object candidate group is displayed, in accordance with one embodiment of the present invention.

FIG. 14 is a flowchart illustrating an ultrasonic image processing method in which, when an object candidate group is selected, measured data of the selected object candidate group is displayed, in accordance with one embodiment of the present invention.

First, volume data of an area around the uterus may be acquired through the data acquisition unit 110 (Operation 300). The area around the uterus may include the inside of the uterus and an area at the outside of the uterus where implantation of a fertilized egg is possible. The area around the uterus where volume data are acquired may be set by controlling a scan angle and a scan depth.

Object candidate groups may be extracted from the acquired volume data (Operation 310). A plurality of object candidate groups may be extracted. Hereinafter, it will be assumed that object candidate groups are extracted. Extraction of the object candidate groups may be carried out by digitizing brightness or shape data of the object candidate groups using the volume data and comparing the acquired brightness or shape values to a reference value. The reference value means a digitized value of brightness or shape of a general fertilized egg which is displayed in an ultrasonic image. Forms having brightness or shape values within an error range of the reference value may be extracted as object candidate groups, and the error range may be arbitrarily determined through external input by a user or arithmetic operation within the apparatus.

The rankings of similarity of the extracted object candidate groups to an actual fertilized egg may be displayed (Operation 320). The rank of an object candidate group is proportional to the likelihood that the object candidate group is an actual fertilized egg. Display of the similarity rankings may help a user to confirm the similarity rankings and understood the accurate position of the fertilized egg.

The user may determine whether or not one of the object candidate groups is selected based on the displayed rankings (Operation 330). If the user does not select one of the object candidate groups, ultrasonic image processing is terminated only by displaying the object candidate groups and the accuracy rankings thereof.

If the user selects one of the object candidate groups, next operation is carried out. That is, measured data of the selected object candidate group may be displayed (Operation 340). The displayed measured data may include volumes, lengths or CRLs of a G-sac, a Y-sac, etc. Further, the displayed measured data may be determined through user selection. Selection of an object candidate group the most proximity to the actual fertilized egg from the object candidate groups as an object and display of various pieces of information of the selected object candidate group help the user to confirm whether or not ectopic pregnancy occurs and to take proper measures.

Figure 15:
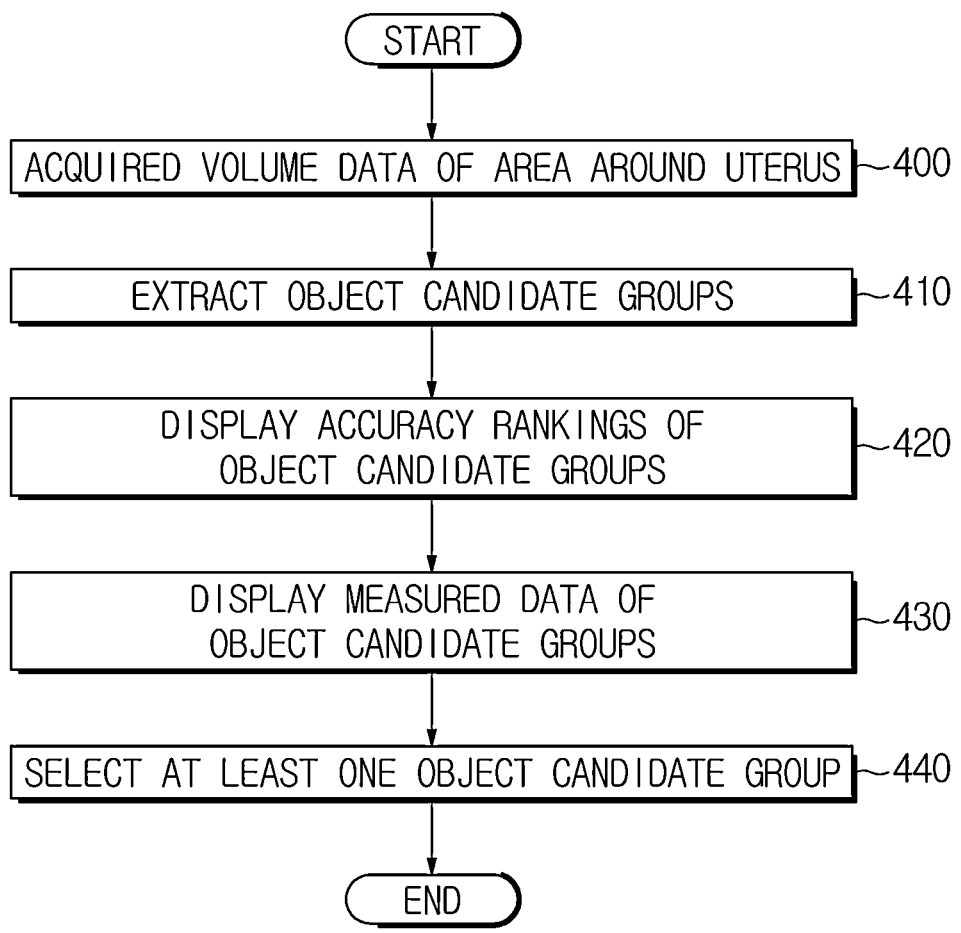
FIG. 15 is a flowchart illustrating an ultrasonic image processing method in which measured data of object candidate groups is displayed and a user selects an object based on the measured data, in accordance with another embodiment of the present invention.

FIG. 15 is a flowchart illustrating an ultrasonic image processing method in which measured data of object candidate groups is displayed and a user selects an object based on the measured data, in accordance with another embodiment of the present invention. Differently from the ultrasonic image processing method of FIG. 14, the ultrasonic image processing method of FIG. 15 may display both object candidate groups and measured data of the object candidate groups.

First, volume data of an area around the uterus is acquired (Operation 400). As described above, the area around the uterus may include the inside of the uterus and an area at the outside of the uterus where implantation of a fertilized egg is possible. The range of such an area may be set by the inside or outside of the ultrasonic image processing apparatus.

One or more object candidate groups may be extracted based on the acquired volume data (Operation 410). Hereinafter, extraction of object candidate groups in the unit of a group will be described. A form having data within the error range of data of an actual fertilized egg may be extracted as an object candidate group.

The accuracy rankings of the extracted object candidate groups are displayed (Operation 420). That is, the rankings of similarity of brightness or shape data of the object candidate groups to the data of the actual fertilized egg serving as a reference value are determined and displayed. Such determined rankings mean the accuracy rankings as to whether or not the object candidate groups correspond to the actual fertilized egg, Differently from the ultrasonic image processing method of FIG. 14, the ultrasonic image processing method in accordance with this embodiment displays the measured data of the object candidate groups together with the object candidate groups (Operation 430). For example, the measured data of the object candidate groups, such as volumes, lengths or CRLs of a G-sac, a Y-sac, etc., are displayed. These measured data serve as basic data to increase accuracy in selection of an object candidate group suspected to be a fertilized egg by a user.

With reference to the measured data displayed together with the rankings, the user selects one or more object candidate groups as objects (Operation 440). Since the selected object candidate group means a fertilized egg, the user may judge whether or not ectopic pregnancy occurs and properly cope with ectopic pregnancy.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An ultrasonic image processing method comprising:
  acquiring, by a probe, volume data from radiating ultrasonic waves to an area around the uterus including an inside of the uterus and an outside of the uterus;
  extracting, by a processor, a plurality of object candidate groups existing in the area around the uterus from the acquired volume data by using a shape or a brightness;
  displaying, by a display unit, the ultrasonic image based on the volume data and distinguishing the extracted plurality of object candidate groups on the area around the uterus in the ultrasonic image displayed;
  determining accuracy rankings of the extracted plurality of object candidate groups; and
  displaying the plurality of object candidate groups in the ultrasonic image and accuracy rankings of the plurality of object candidate groups; and
  selecting, by an input unit, at least based on measured data and the accuracy rankings of the plurality of object candidate groups, one or more object candidate groups among the plurality of object candidate groups with the respective accuracy rankings, and confirming, based on the measured data of the one or more object candidate groups whether or not ectopic pregnancy occurs.

2. The ultrasonic image processing method according to claim 1, wherein, in the acquisition of the volume data, the area around the uterus where the volume data is acquired is set.

3. The ultrasonic image processing method according to claim 1, wherein the acquisition of the volume data is carried out using one of a matrix probe, a 3D probe, and a hands-free 3D probe.

4. The ultrasonic image processing method according to claim 1, wherein the acquisition of the volume data includes acquiring 4D data using the acquired volume data.

5. The ultrasonic image processing method according to claim 1, wherein the displaying the determined accuracy rankings on the ultrasonic image is performed using one of numbers, color, and a table.

6. The ultrasonic image processing method according to claim 1, wherein the distinguishing the extracted plurality of object candidate groups is performed through one of a method of displaying the extracted plurality of object candidate groups in the ultrasonic image by directly marking the extracted plurality of object candidate groups in the ultrasonic image, a method of extracting the extracted plurality of object candidate groups from an ultrasonic image and displaying the extracted plurality of object candidate groups separately from the ultrasonic image, and a method of displaying the extracted plurality of object candidate groups using different rendering.

7. The ultrasonic image processing method according to claim 1, wherein the distinguishing the extracted plurality of object candidate groups in the ultrasonic image includes 2-dimensionally or 3-dimensionally displaying the extracted plurality of object candidate groups.

8. The ultrasonic image processing method according to claim 1, further comprising:
  displaying the measured data of the selected one or more object candidate groups.

9. The ultrasonic image processing method according to claim 1, further comprising:
  displaying the measured data of the displayed plurality of object candidate groups.

10. The ultrasonic image processing method according to claim 8, wherein the measured data includes volumes, lengths, and shapes of display items of the plurality of object candidate groups.

11. The ultrasonic image processing method according to claim 10, wherein the display items of the plurality of object candidate groups include a G-sac, a Y-sac, an amniotic sac, and a CRL.

12. The ultrasonic image processing method according to claim 11, wherein the display items are selected by a user at the outside of an ultrasonic image processing apparatus or are selected by arithmetic operation within the ultrasonic image processing apparatus.

13. The ultrasonic image processing method according to claim 10, wherein the display of the measured data includes acquiring and displaying one of a GA, an EDD, and a risk degree of a pregnant woman based on the measured data.

14. An ultrasonic image processing apparatus comprising:
   a data acquisition unit, including a probe, acquiring volume data of an area around the uterus including an inside of the uterus and an outside of the uterus using ultrasonic waves;
   a data processing unit, including a processor, extracting a plurality of object candidate groups existing in the area around the uterus from the acquired volume data by using a shape or a brightness; and
   a display unit displaying the ultrasonic image based on the volume data, and distinguishing the extracted plurality of object candidate groups on the area around the uterus in the ultrasonic image displayed,
   wherein the data processing unit determines accuracy rankings of the extracted plurality of object candidate groups,
   the display unit displays the plurality of object candidate groups in the ultrasonic image and accuracy rankings of the plurality of object candidate groups, and
   the ultrasonic image processing apparatus further comprises an input unit sensing a user input to select, at least based on measured data and the accuracy rankings of the plurality of object candidate groups, one or more object candidate groups among the plurality of object candidate groups with the respective accuracy rankings, and confirm, based on the measured data of the one or more object candidate groups whether or not ectopic pregnancy occurs.

15. The ultrasonic image processing apparatus according to claim 14, wherein the display unit displays the measured data of the selected object candidate group according to the sensed input.

16. The ultrasonic image processing apparatus according to claim 14, wherein the display unit displays the measured data of the plurality of displayed object candidate groups.

* * * * *